United States Patent [19]

Schubert

[11] 4,184,923

[45] Jan. 22, 1980

[54] REDUCTION OF GENTISIC ACID INTERFERENCE IN ANALYTICAL ELEMENTS

[75] Inventor: Richard M. Schubert, Spencerport, N.Y.

[73] Assignee: Eastman Kodak Company, Rochester, N.Y.

[21] Appl. No.: 848,255

[22] Filed: Nov. 3, 1977

[51] Int. Cl.$^2$ .................. G01N 31/14; G01N 31/22
[52] U.S. Cl. .......................... 435/10; 435/25; 435/28
[58] Field of Search .......... 195/127, 103.5 U, 103.5 R

[56] References Cited

U.S. PATENT DOCUMENTS

| | | | |
|---|---|---|---|
| 3,711,252 | 1/1973 | Roy | 23/230 B X |
| 3,801,466 | 4/1974 | Denney | 195/103.5 R |
| 3,983,005 | 9/1976 | Goodhue et al. | 195/127 X |
| 3,992,158 | 11/1976 | Przybylowicz et al. | 195/103.5 R |
| 4,042,335 | 8/1977 | Clément | 195/103.5 R |
| 4,089,747 | 5/1978 | Bruschi | 195/103.5 R |

Primary Examiner—Raymond N. Jones
Assistant Examiner—Esther M. Kepplinger
Attorney, Agent, or Firm—Ronald P. Hilst

[57] ABSTRACT

Novel elements for the analysis of aqueous liquids which may contain gentisic acid as an interferent are described. Interference of gentisic acid with the analytical test reactions is reduced by using an organic solvent that dissolves the indicator composition but does not preferentially partition gentisic acid into itself from aqueous liquids.

20 Claims, No Drawings

REDUCTION OF GENTISIC ACID INTERFERENCE IN ANALYTICAL ELEMENTS

BACKGROUND OF THE INVENTION

1. Field of the Invention

The present invention relates to elements for the quantitative or semi-quantitative analysis of liquids which may contain gentisic acid as an interferent.

2. Description of the Related Art

It is well known in the art to perform a quantitative or semi-quantitative analysis of a liquid by contacting that liquid with an analytical element containing reagents capable of yielding a detectable product in proportion to the concentration of a predetermined analyte in the liquid. One particularly useful method involves an enzymatic assay wherein the predetermined analyte, upon contact with the analytical element, is oxidized in the presence of an enzyme contained therein to produce a peroxide in proportion to the concentration of the predetermined analyte in the liquid undergoing analysis. A detectable product is then yielded by the reaction of the peroxide with an indicator composition in the presence of a substance having peroxidative activity. This detectable product should be formed in direct proportion to the peroxide present and thus also in proportion to the concentration of the predetermined analyte. Elements and analyses of this type are described in U.S. Pat. No. 3,992,158 and in a copending U.S. application by B. J. Bruschi, Ser. No. 712,972, filed Aug. 9, 1976, both of which are incorporated herein by reference.

Methods of analysis employing reaction mechanisms other than the above-described peroxide mechanism to produce a detectable product are also known. For example, U.S. Pat. No. 3,711,252, describes a method for the quantitative analysis of uric acid in aqueous liquids wherein the aqueous liquid is contacted with a carrier element containing a ferric salt and either 2,4,6-tri(2-pyridyl)-1,3,5-triazine of 2,2':6',2''-terpyride, in a buffered acidic medium. A color change is produced which is directly proportional to the concentration of uric acid in the aqueous liquid.

Additional methods are described in U.S. Pat. No. 3,801,466.

In all of the above-cited references to elements and methods for their use, it is also recognized that substances present in the liquid undergoing analysis other than the predetermined analyte may interfere with or bias the analytical reactions such that the detectable product is not formed in direct proportion to the predetermined analyte alone. This is particularly true for relatively low concentration analytes. For example, in analyses for uric acid or lactic acid in aqueous liquids such as serum or urine, it is recognized that gentisic acid can interfere with the reactions used to indicate the concentrations of uric acid or lactic acid. This is a significant problem, because it is well known that gentisic acid may often be present in liquids such as serum or urine.

Gentisic acid is a metabolic product of acetylsalicylic acid (aspirin) and would be expected to be found in the body fluids of anyone who has recently ingested common aspirin. Its presence has been recognized and methods are available for its analysis in liquids. Since uric acid and lactic acid are normally present in body fluids in relatively small concentrations, the recent ingestion of one or two doses of aspirin can effectively destroy the accuracy of a lactic acid or uric acid analysis.

In some of the analytical methods described above, such as those discussed in U.S. Pat. Nos. 3,711,252 and 3,801,466, gentisic acid is falsely detected as more of the predetermined analyte, because it reacts with the analytical reagents to form the detectable product in the same way that the predetermined analyte does. The result is a false indication that there is a higher concentration of predetermined analyte than is actually present.

Methods are available and known to avoid interferences of this type. For example, U.S. Pat. No. 3,711,252, suggests prevention of gentisic acid interference by incorporation of persulfate in the analytical element. U.S. Pat. No. 3,801,466 suggests a multi-step method of avoidance involving preparation of comparative test samples in one of which the predetermined analyte is totally eliminated by a pre-analysis reaction. The two samples are then analyzed for predetermined analyte, and the difference in results between the two indicates the concentration of interferents such as gentisic acid that may be present. While such methods of avoidance are useful, they are either inconvenient to use (involving multiple steps) or are applicable only to one method of analysis. For example, the use of persulfate suggested by U.S. Pat. No. 3,711,252, would not be successful in avoiding gentisic acid interference with the proxide-linked analyses described previously.

The mechanism of interference of gentisic acid with a peroxide-mechanism-type analysis is quite different from the interferences described above, wherein gentisic acid is falsely detected as predetermined analyte. In a peroxide-mechanism-type analysis, gentisic acid interference produces the opposite effect. It causes a false indication that there is a lower concentration of predetermined analyte than is actually present. Unlike the other analytical methods wherein gentisic acid reacts to form the detectable product just as the predetermined analyte does, in the peroxide-linked analyses gentisic acid competes with the indicator composition in the presence of a substance having peroxidative activity in order to react with the peroxide formed by the interaction of predetermined analyte and enzyme. Thus, less peroxide is available to react with the indicator composition to produce the detectable product, and the concentration of predetermined analyte indicated is falsely low.

Although the mechanism of the competition between the indicator composition and gentisic acid for peroxide is not definitely known, the following hypothesis is presented as a possible explanation of the interference.

In the peroxide-linked analyses which use a analytical element as a test-reagent carrier, all of the test reagents except the liquid being analyzed are usually incorporated into the element itself. The indicator composition may be dispersed or dissolved in a suitable organic solvent within the element. When the liquid to be analyzed is contacted with the analytical element, some of the liquid is imbibed into the element. Any predetermined analyte present in the imbibed liquid then reacts with oxygen in the presence of the enzyme incorporated in the element to produce a peroxide. The peroxide is formed within the element itself and is situated in close proximity to, or interspersed with, the organic solvent containing indicator composition and a substance having peroxidative activity. It is desirable at this point that all of the peroxide formed in the element should act in the presence of the substance having peroxidative activity to oxidize some of the proximately located indicator composition. This oxidation of indicator composition produces a detectable product whose relative concentration is then determined by measuring its optical density spectrophotometrically or otherwise to indicate the concentration of predetermined analyte in the liquid undergoing analysis. It is apparent that any gentisic acid which is situated in similar proximity to the peroxide as is the indicator composition may itself be oxidized by the peroxide. Any peroxide undergoing such reaction is thus made unavailable for oxidation of indicator composition. What is not so apparent is the reason why significant amounts of gentisic acid come to be as well situated for this reaction as is the indicator composition which is dissolved in the organic solvent. Since gentisic acid is originally dispersed throughout the body of the liquid being analyzed, while indicator composition is in organic solvent within the element itself where the peroxide is first formed, one would expect that most peroxide formed would react with indicator composition before it had a chance to come into contact with significant amounts of gentisic acid. However, this is not the case, and it is accordingly hypothesized that the organic solvents previously chosen to facilitate dispersion of the indicator composition within the element, e.g., a solvent such as N,N-diethyl lauramide, which is used in the prior art (see, for example, U.S. Ser. No. 712,972 referred to above), act also to preferentially partition gentisic acid into the organic solvent from the aqueous liquid. This means that a much higher concentration of gentisic acid may be found in the organic solvent than in the aqueous liquid and thus is just as well situated to react with any peroxide being formed as is the indicator composition itself.

Accordingly, it would be desirable to provide an analytical element using the peroxide-linked assay mechanism wherein gentisic acid is not preferentially partitioned into the organic solvent containing indicator composition and is thus not as well situated for reaction with peroxide as is the indicator composition and, therefore, does not interfere with the formation of detectable product to such a significant extent as it does in the analytical elements of the prior art.

SUMMARY OF THE INVENTION

It has been unexpectedly found that certain organic solvents, when used to disperse indicator compositions in analytical elements which utilize the peroxide-linked assay mechanism described above, result in significantly less interfering effects from gentisic acid which may be present in the liquid undergoing analysis.

The present invention, therefore, provides an element for the analysis of a predetermined analyte in an aqueous liquid which may contain gentisic acid as an interferent for the analysis. The element comprises a carrier material permeable to gentisic acid and to the predetermined analyte. Within this carrier are contained test reagents comprising:
(1) an enzyme capable of catalyzing the oxidation of the predetermined analyte to a peroxide,
(2) a substance having peroxidative activity, e.g., peroxidase, and
(3) an indicator composition dispersed in an organic solvent and oxidizable by peroxide in the presence of the substance having peroxidative activity to produce a detectable product.

The present invention reduced the interfering effects of gentisic acid to levels significantly lower than with analytical elements of the prior art by requiring that the organic solvent be chosen from those compounds into which gentisic acid is not preferentially partitioned from an aqueous liquid. It has been unexpectedly found that compounds having the structural formula

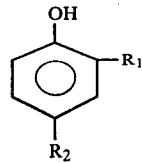

wherein $R_1$ and $R_2$ are straight-chain or branched substituted or unsubstituted alkyl groups, preferably having up to 5 carbon atoms, are useful organic solvents for the present invention because they adequately dissolve the indicator compositions of choice for easy dispersal in the analytical element, yet they do not preferentially partition gentisic acid into themselves from aqueous liquids.

DESCRIPTION OF THE PREFERRED EMBODIMENTS

The present invention is applicable to many kinds of analytical elements well known in the art. Specifically, it is applicable to an element comprising a carrier material permeable to gentisic acid and to a predetermined analyte (the substance being analyzed for). The carrier may be a single layer of material or may be multi-layered, containing such layers as reagent layers, reflecting layers, spreading layers, blocking layers, filter layers, registration layers, support layers, subbing layers, and any other layers known in the related art. Examples of such analytical elements are disclosed, for instance, in U.S. Pat. No. 3,992,158, incorporated herein by reference.

If a particular element is designed to assay a predetermined analyte by first reacting the predetermined analyte with another compound (usually oxygen in the presence of an enzyme) to produce a peroxide, and then reacting this peroxide with an indicator composition dispersed or dissolved in an organic solvent within the element to produce a detectable product, gentisic acid present in the liquid being analyzed may compete for peroxide and destroy the accuracy of the analysis. This effect can be avoided or significantly reduced by the practice of the present invention, that is, by employing an organic solvent adequate to achieve the desired dispersal of the indicator composition that does not also preferentially partition gentisic acid into itself from the aqueous liquid being analyzed. These are the criteria for choosing organic solvents useful in the practice of the present invention.

One class of useful organic solvents includes compounds having the structural formula

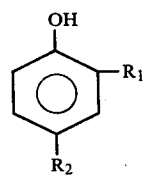

wherein $R_1$ and $R_2$ are substituted or unsubstituted straight-chain or branched alkyl groups. Specific examples include 2,4-di-n-pentylphenol and 2,4-di-t-pentylphenol, among others. These compounds are capable of dissolving many indicator compositions useful in analytical elements, yet do not preferentially partition gentisic acid into themselves from aqueous liquids.

As described above, the invention is applicable to analyses which utilize an indicator composition in organic solvent to react with peroxide to produce a detectable product. Such indicator compositions are numerous and well known in the field of quantitative analysis. They are chosen for their capability to be oxidized by a peroxide in the presence of a substance having peroxidative activity, e.g., peroxidase, to yield a detectable product. They may be single or multi-component indicator compositions. Particularly useful indicator compositions are leuco dyes such as triarylimidazoles of the formula

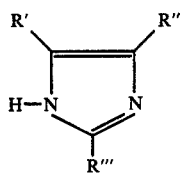

wherein, R', R", and R'" are each aryl or substituted aryl groups of up to 18 carbon atoms, such that at least one of R', R", R'" is an ortho or para hydroxy substituted aryl group, and at least one other of R', R", and R'" has an ortho or para electron donating substituent group.

These and other useful indicator compositions are described more fully in a copending U.S. application by B. S. Bruschi, Ser. No. 712,972, filed Aug. 9, 1976, now U.S. Pat. No. 4,089,747, incorporated herein by reference. This reference and U.S. Pat. No. 3,992,158 also describe methods of measuring the concentration of detectable product formed during the analysis that are useful in working with the elements of this invention, e.g., spectrophotometric measurement of the optical density at a particular wavelength of the detectable product formed within the element.

An additional reagent required in elements of this invention is a compound (usually an enzyme) capable of catalyzing the oxidation of the predetermined analyte to yield a peroxide in the presence of oxygen. This compound is, of course, chosen according to the particular analyte being assayed. Compounds of this type are well known. For example, in an analytical element for the assay of uric acid in aqueous liquids a useful enzyme is uricase, and in an analytical element for the assay of lactic acid in aqueous liquids a useful enzyme is lactate oxidase.

The element may also contain additional substances if desired, such as reactant stabilizers, buffers, mordants, etc.

As mentioned previously, all of these reagents are contained in a carrier layer or layers which together with any other desired layers comprise the elements of this invention. The carrier must be a material permeable to the liquid being analyzed and especially permeable to the predetermined analyte and to gentisic acid, and may be chosen according to such criteria. Well-known useful carrier materials include gelatin, gelatin derivatives, cellulose derivatives, polysaccharides, acrylamides, poly(vinyl alcohol), and poly(vinyl pyrrolidone), among others.

Materials useful for other layers such as spreading, reflecting, blocking, subbing, support, filtration, or registration layers, which may also be included in the element if desired, are described in U.S. Pat. No. 3,992,158. This reference also describes methods useful in the fabrication of such elements.

The following examples are provided to further illustrate specific embodiments of the practice of the present invention and their usefulness in avoiding or reducing gentisic acid interference.

EXAMPLE 1

Effect of 2,4-di-n-pentylphenol in Reducing Gentisic Acid Interference

Two elements were prepared as follows:
Polyethylene terephthalate film supports were coated with registration layers comprising deionized gelatin (10.8 g/m$^2$), peroxidase (6500 U/m$^2$), uricase (215 U/m$^2$), 2(3',5'-dimethoxy-4'-hydroxyphenyl)-4,5-bis(4'-dimethylaminophenyl)imidazole (0.134 g/m$^2$), boric acid (0.323 g/m$^2$), and N,N-diethyl lauramide (2.15 g/m$^2$) in coating #1, or 2,4-di-n-pentylphenol (2.15 g/m$^2$) in coating #2. A gel pad comprising deionized gelatin (5.4g/m$^2$) and boric acid (0.161 g/m$^2$) was applied over each of the previously described layers. A subbing layer comprising poly-n-isopropylacrylamide and a spreading-reflecting layer comprising cellulose acetate (6.6 g/m$^2$) and TiO$_2$ (46.0 g/m$^2$) were then applied.

The elements were evaluated for uric acid concentration. Uric acid solutions with and without added gentisic acid (2.0 mg/dl) were compared. The results, shown in Table 1, indicate a 3–7 fold reduction in bias using the pentylphenol compound.

Table 1

| | Test Element | | | |
|---|---|---|---|---|
| | (di-n-pentylphenol) | | (diethyl lauramide) | |
| Actual Uric Acid Level (mg/dl) | Change in Measured Uric Acid Level With 2.0 mg/dl Gentisic Acid | Bias % | Change in Measured Uric Acid Level With 2.0 mg/dl Gentisic Acid | Bias % |
| 1.0 | 0.0640 | −6.4 | 0.4473 | −45 |
| 5.0 | 0.336 | −6.7 | 1.2221 | −24 |
| 10.0 | 0.5325 | −5.3 | 1.7004 | −17 |

EXAMPLE 2

Reduced Gentisic Acid Interference Upon Increasing the 2,4-di-n-pentylphenol Level Elements were prepared in the same manner as in coating #2 of Example 1 except that the 2,4-di-n-pentylphenol level was increased from 2.15 g/m$^2$, to 3.23 g/m$^2$, and to 4.30 g/m$^2$. The elements were evaluated in the same manner as in Example 1. The results, shown in Table 2, indicate a lower bias at higher levels of uric acid using increased amounts of the organic solvent.

Table 2

| | Solvent Level in Test Element | | | | | |
|---|---|---|---|---|---|---|
| | (2.15 g/m²) | | (3.23 g/m²) | | (4.30 g/m²) | |
| Actual Uric Acid Level (mg/dl) | Change in Measured Uric Acid Level with 2.0 mg/dl Gentisic Acid | Bias % | Change in Measured Uric Acid Level with 2.0 mg/dl Gentisic Acid | Bias % | Change in Measured Uric Acid Level with 2.0 mg/dl Gentisic Acid | Bias % |
| 1.0 | 0.0640 | −6.4 | 0.1067 | −10.7 | 0.1134 | −11 |
| 5.0 | 0.3336 | −6.7 | 0.2576 | −5.2 | 0.2100 | −4.2 |
| 10.0 | 0.5325 | −5.3 | 0.4976 | −5.0 | 0.3168 | −3.2 |

EXAMPLE 3

Analogous Behavior In Controlling Gentisic Acid Interference With 2,4-Di-t-pentylphenol Substituted for 2,4-Di-n-pentylphenol Two elements were prepared in the same manner as in coating #2 of Example 1 except that 2,4-di-n-pentylphenol was replaced with 2,4-di-t-pentylphenol (2.15 g/m²) in one element. The elements were then evaluated as above. The results in Table 3 show analogous behavior of the branched-chain and straight-chain dispersion materials.

Table 3

| | Test Element | | | |
|---|---|---|---|---|
| | (di-n-pentylphenol) | | (di-t-pentylphenol) | |
| Actual Uric Acid Level (mg/dl) | Change in Measured Uric Acid Level with 2.0 mg/dl Gentisic Acid | Bias % | Change in Measured Uric Acid Level with 2.0 mg/dl Gentisic Acid | Bias % |
| 1.0 | 0.007 | −0.7 | 0.015 | −1.5 |
| 5.0 | 0.212 | −4.2 | 0.306 | −6.1 |
| 10.0 | 1.022 | −10 | 1.172 | −12 |

The invention has been described in detail with particular reference to certain preferred embodiments thereof, but it will be understood that variations and modifications can be effected within the spirit and scope of the invention.

What is claimed is:

1. In an element for the analysis of a predetermined analyte in an aqueous liquid which may contain gentisic acid, said element comprising a carrier permeable to gentisic acid and permeable to said predetermined analyte, said carrier containing reagents comprising:
   (a) an enzyme capable of catalyzing the oxidation of said predetermined analyte to a peroxide,
   (b) a substance having peroxidative activity, and
   (c) an indicator composition dispersed in an organic solvent and oxidizable by said peroxide in the presence of said substance having peroxidative activity to produce a detectable product;
the improvement wherein said organic solvent comprises a compound into which gentisic acid is not preferentially partitioned from the aqueous liquid.

2. In an element for the analysis of a predetermined analyte in an aqueous liquid which may contain gentisic acid, said element comprising a carrier permeable to gentisic acid and permeable to said predetermined analyte, said carrier containing reagents comprising:
   (a) an enzyme capable of catalyzing the oxidation of said predetermined analyte to a peroxide,
   (b) a substance having peroxidative activity, and
   (c) an indicator composition dispersed in an organic solvent and oxidizable by said peroxide in the presence of said substance having peroxidative activity to produce a detectable product;
the improvement wherein said organic solvent comprises a compound having the structural formula

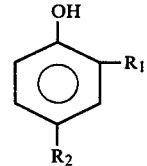

wherein $R_1$ and $R_2$ are substituted or unsubstituted straight-chain or branched-chain alkyl groups.

3. An element as described in claim 2 wherein the organic solvent is selected from the group consisting of 2,4-di-n-pentylphenol and 2,4-di-t-pentylphenol.

4. An element as described in claim 2 wherein the substance having peroxidative activity is peroxidase.

5. An element as described in claim 2 wherein the indicator composition is a leuco dye.

6. An element as described in claim 5 wherein the leuco dye is a triarylimidazole of the formula

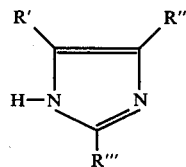

wherein R', R", and R''' are each aryl or substituted aryl groups of up to 18 carbon atoms, such that at least one of R', R", and R''' is an ortho or para hydroxy substituted aryl group, and at least one other R', R", and R''' has an ortho or para electron donating substituent group.

7. An element as described in claim 6 wherein the leuco dye is 2(3',5'-dimethoxy-4'-hydroxyphenyl)-4,5-bis(4'-dimethylaminophenyl)imidazole.

8. An element as described in claim 2 wherein said predetermined analyte is uric acid and said enzyme is uricase.

9. An element as described in claim 2 wherein said predetermined analyte is lactic acid and said enzyme is lactate oxidase.

10. An element as described in claim 2 wherein said reagents further comprise a compound for adjusting pH.

11. An element as described in claim 2 wherein said carrier comprises a hydrophilic colloid selected from the group consisting of gelatin, a gelatin derivative, a cellulose derivative, a polysaccharide, an acrylamide, poly(vinyl alcohol), and poly(vinyl pyrrolidone).

12. An element as described in claim 11 wherein said carrier is coated on a support material.

13. An element as described in claim 11 wherein a spreading-reflecting layer is coated over said carrier.

14. An element as described in claim 13 wherein said carrier is coated on a support material.

15. An element as described in claim 14 wherein a layer comprising gelatin and a compound for adjusting pH is overcoated with a subbing layer and is interposed between said carrier and said spreading-reflecting layer.

16. An element for the analysis of uric acid in an aqueous liquid which may contain gentisic acid, said element comprising a carrier permeable to gentisic acid and to uric acid, said carrier containing reagents comprising:
(a) uricase,
(b) peroxidase, and
(c) a leuco dye dispersed in an organic solvent having the structural formula

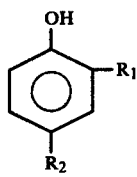

wherein $R_1$ and $R_2$ are straight-chain or branched alkyl groups.

17. An element for the analysis of uric acid as described in claim 16 wherein the carrier is gelatin, the organic solvent is selected from the group consisting of 2,4-di-n-pentylphenol and 2,4-di-t-pentylphenol, the leuco dye is 2(3',5'-dimethoxy-4'-hydroxyphenyl)-4,5-bis(4'-dimethylaminophenyl) imidazole, and the reagents further comprise a compound for adjusting pH.

18. An element for the analysis of uric acid as described in claim 17 wherein said gelatin carrier is coated on a support material, a layer comprising gelatin and boric acid is coated on said gelatin carrier and is itself overcoated with a subbing layer, and said subbing layer is overcoated with a spreading-reflecting layer.

19. An element for the analysis of uric acid as described in claim 18 wherein said support material comprises polyethylene terephthalate, said subbing layer comprises poly-n-isopropylacrylamide, and said spreading-reflecting layer comprises cellulose acetate and titanium dioxide.

20. An element for the analysis of lactic acid in an aqueous liquid which may contain gentisic acid, said element comprising a carrier permeable to gentisic acid and to lactic acid, said carrier containing reagents comprising:
(a) lactate oxidase,
(b) peroxidase, and
(c) a leuco dye dispersed in an organic solvent having the structural formula

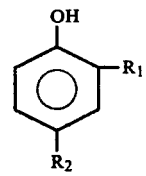

wherein $R_1$ and $R_2$ are straight-chain or branched alkyl groups.

* * * * *